(12) United States Patent
Szanto

(10) Patent No.: US 8,518,045 B2
(45) Date of Patent: Aug. 27, 2013

(54) SPHERICAL OSTEOTOMY DEVICE AND METHOD

(76) Inventor: Zsigmond Szanto, Twin Falls, ID (US)

(*) Notice: Subject to any disclaimer, the term of this patent is extended or adjusted under 35 U.S.C. 154(b) by 0 days.

(21) Appl. No.: 13/136,243

(22) Filed: Jul. 26, 2011

(65) Prior Publication Data

US 2011/0288555 A1 Nov. 24, 2011

Related U.S. Application Data

(62) Division of application No. 12/211,063, filed on Sep. 15, 2008.

(60) Provisional application No. 60/993,820, filed on Sep. 13, 2007.

(51) Int. Cl.
*A61F 2/46* (2006.01)
(52) U.S. Cl.
USPC ............. 606/86 R; 606/79; 606/82; 606/176; 606/177
(58) Field of Classification Search
USPC ..................................... 606/79–99
See application file for complete search history.

(56) References Cited

U.S. PATENT DOCUMENTS

| | | | |
|---|---|---|---|
| 2,210,623 A | 8/1940 | Kelly | |
| 4,069,824 A | 1/1978 | Weinstock | |
| 4,349,058 A | 9/1982 | Comparetto | |
| 4,952,214 A | 8/1990 | Comparetto | |
| 4,955,888 A | 9/1990 | Slocum | |
| 5,092,050 A | 3/1992 | Bardeen | |
| 5,122,142 A | 6/1992 | Pascaloff | |
| 5,169,401 A | 12/1992 | Lester et al. | 606/79 |
| 5,318,570 A * | 6/1994 | Hood et al. | 606/99 |
| 5,514,141 A | 5/1996 | Prizzi | |
| 5,566,458 A * | 10/1996 | Bednar | 30/392 |
| 5,643,270 A * | 7/1997 | Combs | 606/79 |
| 6,190,390 B1 | 2/2001 | McAllister | |
| 6,238,126 B1 | 5/2001 | Dall | |
| 6,375,684 B1 | 4/2002 | Kriek | |

(Continued)

FOREIGN PATENT DOCUMENTS

| | | | |
|---|---|---|---|
| DE | 19723718 A | * | 12/1998 |
| DE | 19723718 A1 | | 12/1998 |

(Continued)

OTHER PUBLICATIONS

Principles of Deformity Correction, Dror Paley, Springer-Verlag, 2003, Berlin Germany.
Principles of Uniapical and Biapical Radial Deformity Correction Using Dome Osteotomies and the Center of Rotation of Angulation Methodology in Dogs. Abstract, Derek B. Fox, DVM, PhD, Diplomate ACVS, James L. Tomlinson, DVM, MVSci, Diplomate ACVS, James L. Cook, DVM, PhD, Diplomate ACVS, and Lee M. Breshears, DVM. Veterinary Surgery, 35:67-77, 2006.

(Continued)

*Primary Examiner* — Sameh Boles
*Assistant Examiner* — Samuel Hanna
(74) *Attorney, Agent, or Firm* — TraskBritt

(57) ABSTRACT

A spherical osteotomy device for the efficient surgical sectioning of bone includes a part spherical body and a shank. The part spherical body includes an outer surface, an inner surface, a cutting end between the outer surface and the inner surface, an axis extending from the outer surface through the inner surface, and an origin on the axis. The inner surface has a substantially constant radius extending from the origin. The shank extends outwardly from the outer surface of the body and is substantially aligned with the axis. Other embodiments of an osteotomy device are described. Also provided is a method of using the osteotomy device for performing spherical osteotomies.

13 Claims, 14 Drawing Sheets

(56) References Cited

U.S. PATENT DOCUMENTS

| | | | |
|---|---|---|---|
| 6,485,495 B1 * | 11/2002 | Jenkinson | 606/84 |
| 7,189,036 B1 | 3/2007 | Watson | 408/204 |
| 2005/0130774 A1 | 6/2005 | Wohfeil | |
| 2005/0273112 A1 | 12/2005 | McNamara | |
| 2006/0229621 A1 | 10/2006 | Cadmus | |
| 2008/0287954 A1 | 11/2008 | Kunz et al. | |
| 2009/0076513 A1 | 3/2009 | Szanto | |
| 2010/0234844 A1 | 9/2010 | Edelhauser et al. | |

FOREIGN PATENT DOCUMENTS

| | | |
|---|---|---|
| WO | 2006-059120 | 6/2006 |
| WO | WO 2009/035670 A2 | 3/2009 |
| WO | WO 2009/035670 A3 | 3/2009 |

OTHER PUBLICATIONS

International Preliminary Report on Patentability for PCT/US2008/010672, mailed Mar. 25, 2010, 9 pages.
PCT International Search Report for International Application No. PCT/US2008/010672, mailed Apr. 13, 2009, 4 pages.
PCT Written Opinion for International Application No. PCT/US2008/010672, mailed Apr. 13, 2009, 6 pages.
Introduction to Spherical Geometry (last modified Apr. 28, 2011).
Spherical Geometry—EscherMath, visited Feb. 31, 2011.
The Geometry of the Sphere 1.-3., visited Feb. 31, 2011.
Weisstein, "Spherical Geometry" from MathWorld-A Wolfram Web Resource, visited Feb. 31, 2011.

* cited by examiner

SPHERICAL OSTEOTOMY DEVICE AND METHOD

CROSS-REFERENCE TO RELATED APPLICATIONS

This application is a divisional of U.S. patent application Ser. No. 12/211,063, filed Sep. 15, 2008, pending, which claims the benefit under 35 USC §119 (e) of U.S. Provisional Patent Application Ser. No. 60/993,820 filed Sep. 13, 2007, the disclosure of each of which is hereby incorporated herein in its entirety by this reference.

FIELD OF INVENTION

This invention relates generally to osteotomy devices for use in the surgical cutting of bones, and more specifically to spherical osteotomy devices for use in surgical division or sectioning of bones and a method therefore, particularly spherical osteotomy devices for use in performing "true dome" osteotomies.

BACKGROUND

Osteotomy is defined as a procedure for surgical division or sectioning of a bone. Displacement osteotomy is the surgical division of a bone and shifting of the divided ends to change the alignment of the bone or to alter weight-bearing stresses. This procedure is typically utilized by orthopedic surgeons to correct for malalignment and malorientation, including uniapical and multiapical deformities of the bone, as well as the treatment for compartmental diseases. The goal of displacement osteotomies is to create congruent matching surfaces to align, stabilize, and maximize contact between the corresponding bone sections. Osteotomies may include a number of different types of bone sectioning procedures that result in two corresponding sections of the bone which are then reoriented until a desired alignment between the bone sections is achieved. In order to improve stability, distribute the load evenly, eliminate abnormal stress, and aid healing, surgeons strive to maximize the match or contact area between two corresponding surfaces when surgically sectioning the bone. Representative types of bone cuts include simple transverse, obliqued cuneiform, stairstep, simple to complex wedges, barrel-vault, and dome shaped cuts. In practice, a surgeon may choose a specific cut configuration in order to achieve a particular reconfiguration of the bone being treated.

Although so called "dome osteotomy" has been known for decades, the term "dome osteotomy" has been used to refer conventionally to semi-cylinder, i.e., half or part (partially) cylindrical, shaped surgical cuts. Specifically, amongst experts within the field, "cylindrical osteotomy" would be a more accurate descriptor for these types of so called "dome"osteotomies, as it is well understood by all to be a cylindrically shaped cut. Although resulting shapes of so called "dome" osteotomy are not domes, the following terms have been used in the scientific literature to refer to osteotomies wherein corresponding bone cuts are shaped like a semi-cylinder: dome, spherical, barrel-vault, focal dome (reversed dome), crescentic, and arcuate. These conventional forms of semi-cylindrically shaped osteotomies are better described as barrel-vault osteotomies, and will be described accordingly herein below. Further, the term "dome osteotomy" has been used in the literature and within the field of corrective osteotomy to describe barrel-vault osteotomy, however, the field of corrective osteotomy has lacked a method and device to accomplish, as described below with respect to the invention herein presented, what will be termed "true dome" or spherical osteotomy.

In barrel-vault osteotomy, a bone is sectioned by oscillating a saw blade around the central axis of the cylinder while cutting the bone. Barrel-vault osteotomy may be used to correct angulation about the central axis of the cylindrical cut and translation along the central axis of the cylindrical cut. The barrel-vault osteotomy provides and allows correction in two-dimensions, which sometimes results in undesirable secondary translation because of imparted limitation of two-dimensional repositioning of the bone portions. In this respect, barrel-vault osteotomy cannot be used to correct axial rotations of the bone without creating gaps and instability between bone segments thereby being a major limitation of so called "barrel-vault" osteotomies. The success of barrel-vault osteotomies relies heavily on meticulous pre-operative planning, and while it may be used to correct radial deformities in the frontal and sagittal planes, one of its major disadvantages is the limited ability to correct axial rotational deformities. Accordingly, it would be desirable to provide a device capable of cutting a bone into corresponding sections that allows for correction in more than two dimensions.

There are a variety of devices and methods available to accomplish these so called "barrel-vault" osteotomies. One method includes drilling a series of holes in the bone along a planned arc. In one example, U.S. Pat. No. 6,190,390 discloses an apparatus and method for the surgical realignment of the knee through proximal tibial osteotomy. The apparatus has an arcuate profile configuration for establishing a series of parallel holes forming the desired semi-cylindrical contour of the barrel-vault cut. In addition to the general disadvantages of "barrel-vault" osteotomies mentioned above, such a method undesirably creates ridges between adjacent sets of drilled parallel holes making alignment more difficult and gaps between bone portions more probable.

According to another example, U.S. Pat. No. 4,955,888 discloses a biradial saw blade with an arcuate body, powered by oscillating motion that is used to create the barrel-vault osteotomy. Such saw blades are typically associated with a saw assembly which operates to displace the blade in a reciprocating motion by oscillating the blade around the drive axis of the saw assembly. The saw blade has a curved cutting edge at the end of the body shaped as a part of a cylinder for making barrel-vault shaped surgical cuts. While the cut resulting from the use of the biradial saw blade provides for a better match of the two surfaces of both bone portions, the heat and friction produced by the saw blade may be detrimental to the bone, specifically for allowing proper healing thereof. Also, other conventional "barrel-vault" saw blades may include a partially cylindrically shaped body having a cutting member on its leading edge.

Conventional blades are limited in providing semi-cylindrical cuts of the bone, which limit the correction in the bone, particularly when correcting deformities that lie in two planes, such as the frontal and sagittal planes. Correction of deformities in two planes requires meticulous preoperative planning in order to determine the central axis about which the cut in the bone is to be made. This is especially crucial if the bone portions are to be properly positioned to correct the deformity. Cutting the bone about a different central axis will only allow, at best, partial correction in the two planes. Further, it is desirable to provide improvement for the correction of malalignment, malorientation and compartmental disease, including other deformities of the bone by osteotomy procedures and tools. Accordingly, it would be desirable to provide an osteotomy tool for cutting bone that increases the adjustability of the bone portions, achieves optimal bone contact, and improves primary stability. It is also desirable to provide an osteotomy tool that is less dependent upon cutting the bone precisely about a determined central axis when attempting to achieve proper correction.

Another disadvantage associated with the use of so-called "barrel-vault" osteotomies is the limited ability to correct axial rotational deformities. Correction of other deformities may also be difficult to make, particularly when a correction of the deformity requires cutting the bone in a less accessible location. This makes it increasingly difficult for a surgeon to provide the corrective cut, as described above, where it is needed. Another disadvantage of barrel-vault osteotomies is the bone portions, after severance, may only be repositioned with respect to one another about two principal dimensions, one of the principal dimensions being an angular displacement or rotation about the central axis, and the other principal dimension being a lateral displacement or position along the central axis. The angular displacement or rotation allows the bone pieces to be rotated with respect to one another about the central axis to the desired correction. The lateral displacement or position allows the bone pieces to be positioned with respect to each other along the central axis to the desired correction. Also, the bone pieces may obtain the desired correction through a small combination of lateral displacements and angular displacements. Lateral displacement of the bone pieces is limited to the extent that the bone portions include sufficient surface contact for proper healing to occur. Angular displacement of the bone pieces provides for better bone-to-bone contact than lateral displacement, however, angular displacement is still limited if the bone portions are to be maintained with sufficient surface contact in order to provide for proper healing. Accordingly, it would be desirable to provide improved osteotomy of a bone to allow for greater surface contact between the repositioned cut pieces. It is further desirable to provide an osteotomy tool for severing a bone to provide correction of the bone pieces in more than two dimensions.

U.S. Pat. No. 5,643,270 discloses a multi-plane curvilinear saw to be used with corresponding guide, and particularly adapted for cutting the bones in a digit, and more specifically for shaping the end of a bone in a digit by ostectomy for fusion with another member of a joint in a digit. Ostectomy refers to surgical removal of a bone or part of a bone. The conventional device is specifically designed to work similarly to a surgical chisel removing cartilage and spongy bone from one side of the joint surface. The saw blade includes a hemispherically shaped body having a flat top and a shank extending from the flat top, and a cutting edge along an exposed edge. This conventional device provides the use of a saw guide in order to ensure accuracy, restrict the movement of the cutting teeth to the path defined by the curved slots, and to avoid slipping of the saw and inadvertent cutting of the surrounding tissue. The saw can be delicately translated, tilted and/or rotated to a limited degree about the end of the bone by the surgeon to make the exact cut until the flat portion of the saw rests flat on the guide. The guide is a necessary component, as without it the saw would slide off the end of the bone. A curved shape occurs on the end of the bone, because the cutting edge with its arc is guided by a saw guide about the arcuate path. Whereas the conventional device is advantageous for general ostectomies for shaping the end of a bone, it is impractical for precise osteotomy of a bone. Such conventional devices undesirably require metal to metal contact between the cutting blade and the guide. Orthopedic surgeons try to avoid contact of the saw blade with other materials (such as metal or plastic) in order to protect their instruments (avoid unnecessary wear and galling), to avoid unnecessary heat production and potential thermal necrosis of the underlying tissue, as well as to avoid material shavings getting into the open wound. Moreover, this conventional device and method are not suitable for true dome osteotomies because, while it may create a curvilinear cut partially into the bone, the device would wedge itself between opposing bone portions during the cutting process due to the shape of the sectioning element or blade. Furthermore, the conventional device may damage the bone by creating too much pressure and heat, caused by friction, during the cutting procedure. Moreover, such conventional devices having a flat top on the upper end of the device restrict full cutting or sectioning of the bone into two portions, particularly when the flat top of the device reaches the parallel surface of the guide with respect to the axis of the bone that prevents complete cutting of the bone.

Accordingly, it would be desirable to provide a device capable of cutting a bone into corresponding sections resulting in a "true dome" or spherical osteotomy.

Accordingly, it is also desirable to provide an osteotomy tool and method for "true dome" or spherical osteotomies that result in two substantially congruent (one concave and one convex) surfaces after cutting a bone.

SUMMARY OF THE INVENTION

Accordingly, the invention presented herein accomplishes a substantially spherical or "true dome" shape when cutting bone, facilitating correction in three dimensions and aiding the healing process of the cut bones.

In embodiments of the invention, a "true dome" or spherical osteotomy device may be used to cut a bone into two substantially mating portions, allowing correction of the bone to be accomplished by rotating bone portions about their substantially mating surfaces, which may also allow correction for axial rotation without unnecessary secondary translation. Moreover, "true dome" osteotomy provides for three-dimensional adjustability of the bone while maximizing bone-to-bone surface contact and stability. Advantageously, procedures utilizing the spherical osteotomy device require less complex pre-operative planning and provide more accurate correction.

Embodiments of the invention provide several important advantages. Specifically, a "true dome" or spherical osteotomy device, including a method of using the spherical osteotomy device, may create dome shaped mating surfaces as opposed to semi-cylindrical cuts conventionally made, may provide for match of the proximal and distal fragments of the osteotomy, may optimize dome height, may minimize bone loss, may decrease the complexity of pre-operative planning, may allow the surgeon to make intraoperative adjustments to attain desired correction, may not unacceptably wedge or heat bone portions during cutting, may avoid unnecessary heat and burning, may minimize damage to bone tissue and the surrounding soft tissue, may avoid metal to metal contact of surgical instruments, and may aid faster and more reliable healing of the bone. Another advantage, a spherical osteotomy device may be self-guiding and self-centering within the cut being made in the bone, giving the surgeon options in planning the surgical approach around soft tissue structures.

In one embodiment of the invention, a spherical osteotomy device for the efficient surgical sectioning of bone is described that includes a partially spherical body and a shank. The part spherical body includes an outer surface, an inner surface, a cutting end between the outer surface and the inner surface, an axis that extends from the outer surface through the inner surface, and an origin located on the axis. The inner surface has a substantially constant radius extending from the origin. The shank extends outwardly from the outer surface of the body and is substantially aligned with the axis. Optionally, the spherical osteotomy device may be attached to an osteotome handle or to a power tool such as an oscillating saw. The spherical osteotomy may be used to cut bones or other anatomical structures into two portions in such a way as to facilitate repositioning of oppositely opposed substantially mating surfaces in the desired position or orientation, thereby also to aid healing.

The bone saw bit advantageously allows the bone portions after surgical severance to be repositioned together in at least one of three different degrees of motion, because the bone saw bit cuts a "true dome" osteotomy into each bone portion. One of the bone portions will have a convex surface that substantially mates with the other bone portion having a concave surface. Because the surfaces have mating contours, the bone portions relatively may be rotated about the longitudinal axis of the bone and tilted in either of two dimensions about the bone to achieve repositioning in three dimensions.

Other embodiments of an osteotomy device are described.

Also provided is a method of using the osteotomy device for performing "true dome" or spherical osteotomies. The method of the instant invention involves the following:

(1) Providing a sectioning blade of the type described herein, wherein the sectioning blade is operably secured to a device for oscillating the blade;
(2) Defining a center of rotation in the bone to be sectioned;
(3) Actuating the device to oscillate the blade about the origin of the blade;
(4) Engaging the blade against the bone to be sectioned; and
(5) Sectioning the bone by passing the blade through the bone while rotating the blade about the center of rotation.

In a preferred method the above indicated procedural steps are supplemented by the following additional steps, namely:

(A) Defining a longitudinal axis of the bone to be sectioned;
(B) Defining proximal and distal longitudinal axis lines of the bone to be sectioned;
(C) Finding the intersection of the proximal and distal longitudinal axis lines, denominated as a center of rotation of angulation (CORA);
(D) Generally aligning the origin of the sectioning blade with the CORA by positioning the blade so that the origin of the sectioning blade is at the same location as the point of intersection—in some cases the surgeon can choose an off-set CORA to accomplish the osteotomy;

Steps (A) through (D) are performed subsequent to step (2) above and prior to step (3) above.

In a further embodiment of the instant method, steps A-D are supplemented by a further step (E) wherein step (E) comprises sectioning the bone by passing the blade through the bone while rotating the blade about the center of rotation while retaining the origin of the blade substantially at the defined CORA.

Step (E) is performed simultaneously with step (5) above.

Advantageously, the osteotomy device may be utilized in a variety of surgical procedures beyond "true dome" or spherical osteotomies, such as bone fracture repair in humans and animals.

Other advantages, features and alternative aspects of the invention will become apparent when viewed in light of the detailed description of the various embodiments of the invention when taken in conjunction with the attached drawings and appended claims.

BRIEF DESCRIPTION OF THE DRAWINGS

While the specification concludes with claims particularly pointing out and distinctly claiming that which is regarded as the invention, the advantages of this invention may be more readily ascertained from the following description of the invention when read in conjunction with the accompanying drawings in which:

DETAILED DESCRIPTION OF THE INVENTION

Figure 1:
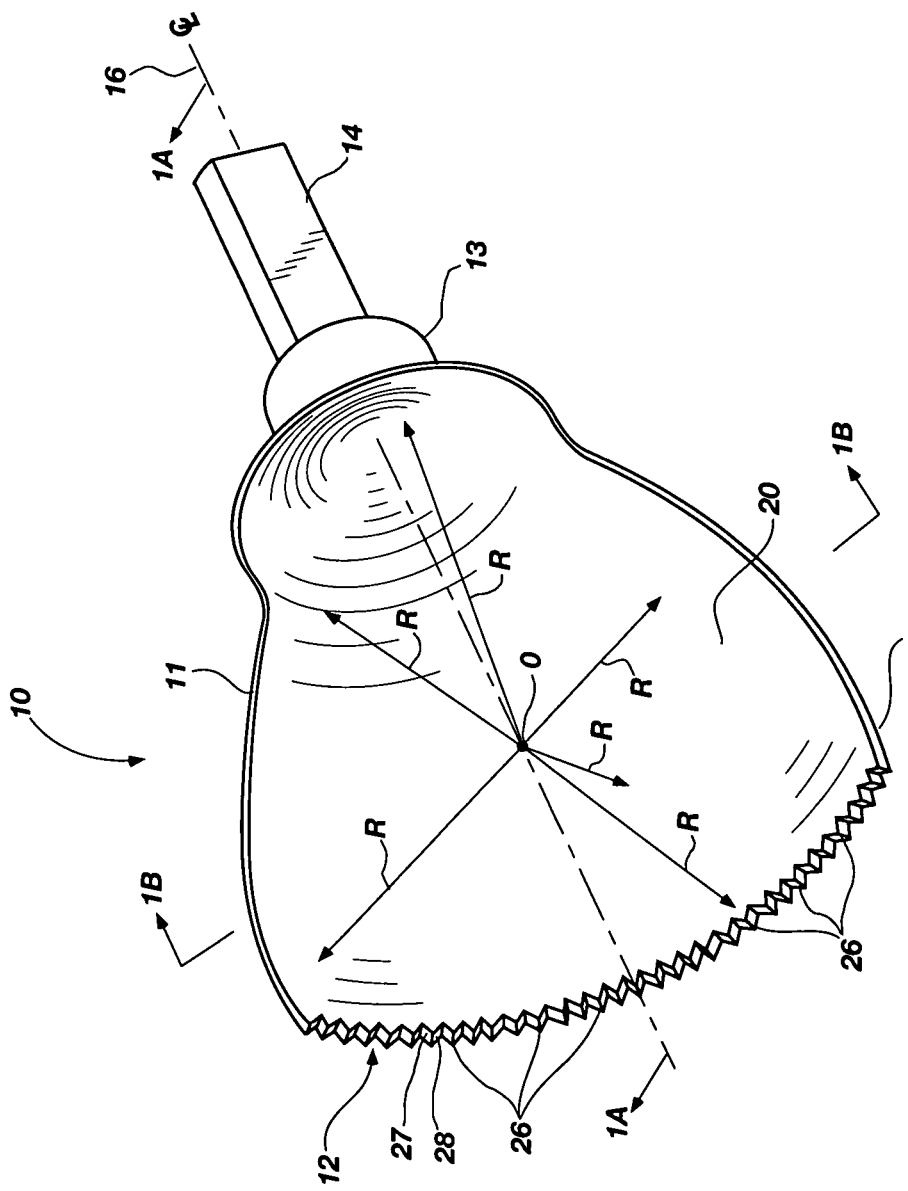
FIG. 1 is a perspective view of a bone saw bit in accordance with an embodiment of the invention.

The illustrations presented herein are, in some instances, not actual views of any particular osteotomy device, "true dome" osteotomy device, spherical osteotomy device, bone saw bit, cutting element, hard facing material or other feature of an osteotomy bit or device, but are merely idealized representations which are employed to describe the invention. Additionally, like elements and features among the various drawing figures are identified for convenience with the same or similar reference numerals.

"True dome" or spherical osteotomy devices, hereinafter "bone saw bits," suitable for osteotomy or other surgical cutting of bone are presented. Bone saw bits for surgically severing bone are now presented together with some terminology to facilitate a proper understanding of the invention.

The term "spherical" as used herein means a characteristic of a sphere over any portion of a sphere and is not to be limited to a complete sphere, including, but not limited to, a hollow spherical structure. Also, the term "spherical" may refer to an inner surface, an outer surface, or an inner surface and an outer surface of a sphere, including partial portions thereof.

The term "part spherical" as used herein means a characteristic of a sphere or a part sphere over any portion of a sphere and is not to be limited to a sphere or part sphere or a hollow sphere. Also, the term "part spherical" may refer to an inner surface, an outer surface, or an inner surface and an outer surface of a sphere or part sphere, including partial portions thereof.

The term "hemispherical" as used herein means a characteristic of a hemisphere over any portion of a hemisphere and is not to be limited to a hemisphere. Also, the term "hemispherical" may refer to an inner surface, an outer surface, or an inner surface and an outer surface of a hemisphere, including partial portions thereof.

As used herein the term "true dome" will be defined as a curved surface, produced by a cutting action, wherein the radius of curvature of that curved surface is constant or substantially constant over the entire curved surface.

Figure 1A:
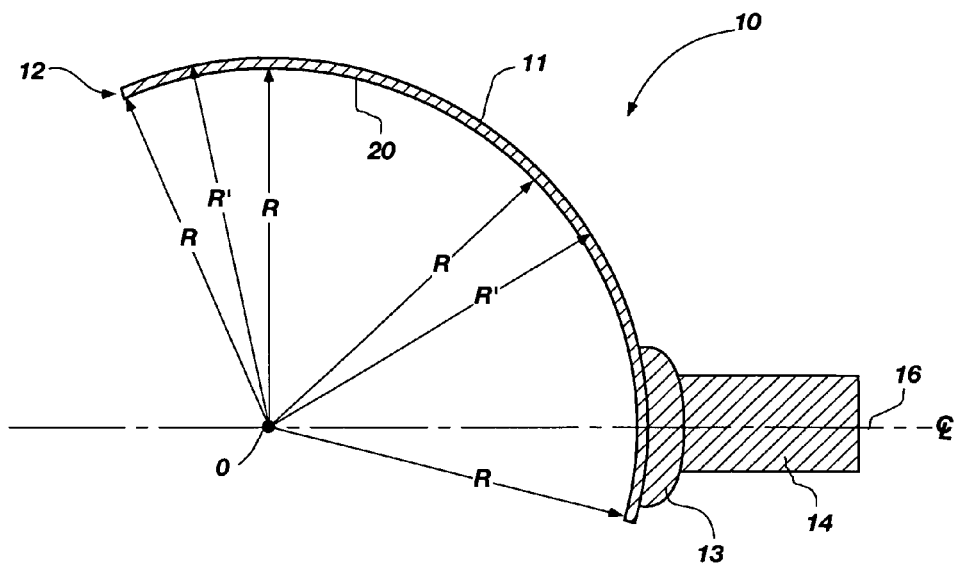
FIG. 1A is a cross sectional view of the bone saw bit of FIG. 1 taken along section line 1A-1A.
Figure 1B:
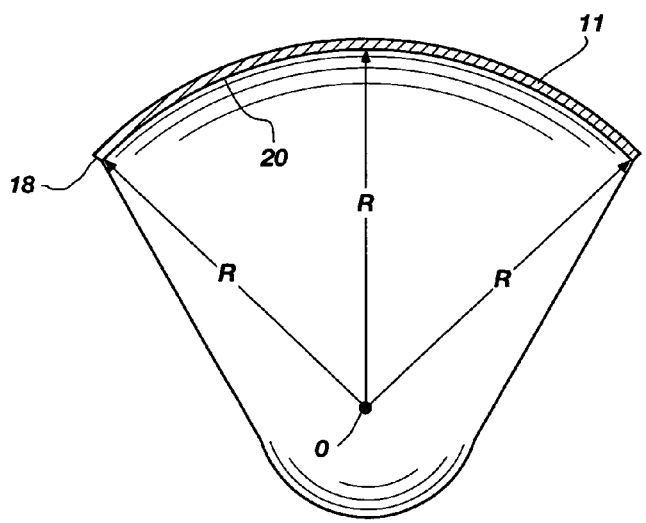
FIG. 1B is a front view of the bone saw bit of FIG. 1.
Figure 2:
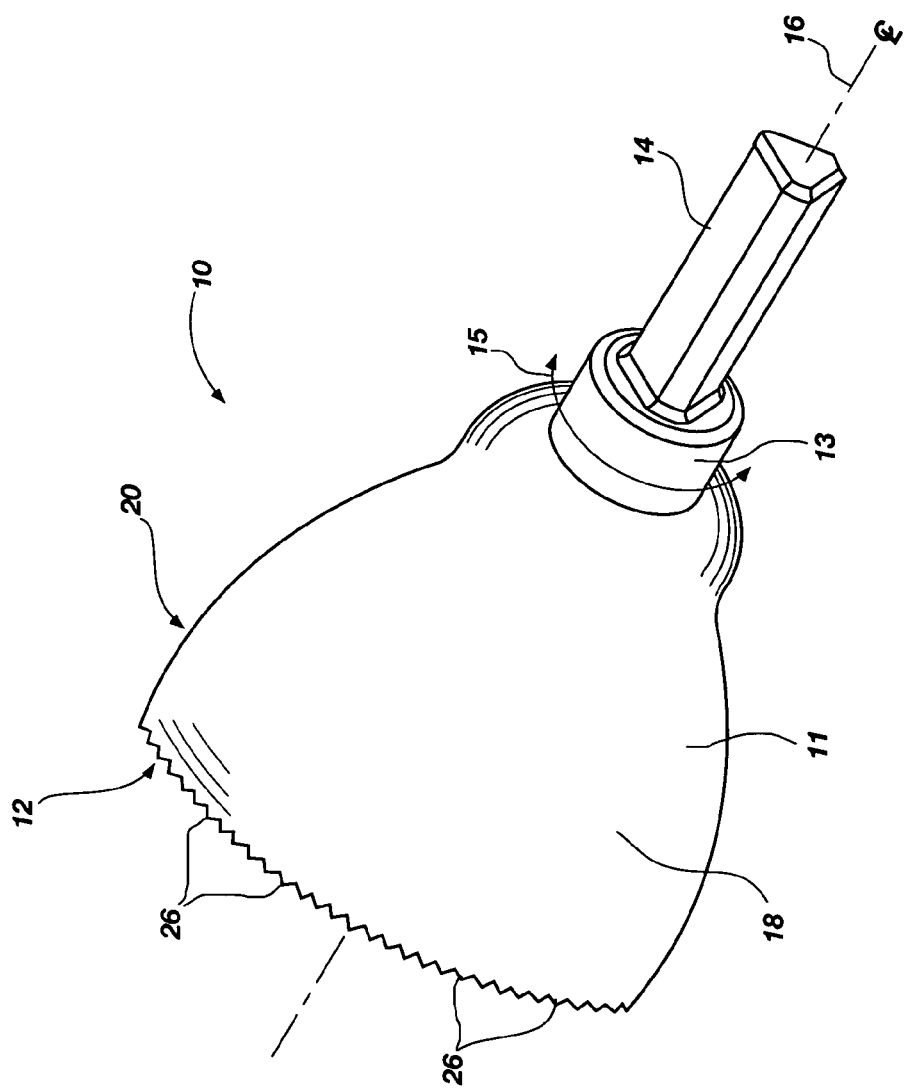
FIG. 2 is another perspective view of the bone saw bit shown in FIG. 1.

FIG. 1 is a perspective view of a device, or bone saw bit, 10 in accordance with an embodiment of the invention. FIGS. 1A and 1B are further views of the bone saw bit 10. Reference may also be made to FIG. 2, which shows another perspective view of the bone saw bit 10. The bone saw bit 10 includes a part spherical body 11 and a cutting end 12, which together form key features of the invention. The part spherical body 11 is made of a suitably rigid material such as surgical steel, and may include other materials suitable for the surgical severance of bone, particularly in aseptic environments.

The bone saw bit 10 provides for the efficient surgical sectioning of bone (described below) and includes the part spherical body 11 having a shank 14 extending therefrom along an axis 16. The shank 14 allows the bone saw bit 10 to be attached to a chuck e.g. a three pronged chuck (not shown), of an oscillating saw (not shown). The oscillating saw rotationally drives the bone saw bit 10, as indicated by the double-ended arrow 15 shown in FIG. 2, to efficiently penetrate a desired member, such as bone, in order to obtain an efficient, optimal or "true" dome on both pieces of the severed member. The dome on one severed member will result in a convex dome, while the dome on the other severed member will result in a concave dome.

The shank 14 may have any attachment connection, such as a threaded stem or a quick release, for example without limitation. The attachment connection will allow the bone saw bit 10 to be attached to any device, such as a power tool or hand operated tool for improved cutting control or usability. Also, while the shank 14 is shown as being integral with the part spherical body 11, the shank 14 may also be a separate member that is coupled to the part spherical body 11. Further, the shank 14 may include a hub 13 (see FIG. 2) as shown.

The part spherical body 11 also includes an outer surface 18, an inner surface 20. The cutting end 12 extends between the outer surface 18 and the inner surface 20. The axis 16 may extend axially inline with the shank 14 and passes from the outer surface 18 through the inner surface 20 of the part spherical body 11. The axis 16 includes an origin or center as indicated by indicia O as labeled. The inner surface 20 is substantially characterized by having a constant radius R extending from the origin O Advantageously, the constant radius R allows the bone saw bit 10 to efficiently and smoothly transition over, and rotate about, the member it is cutting. Further, efficient usage of the bone saw bit 10 is provided for because the outer surface 18 may also be substantially characterized by a constant radius R' over the substantial portion thereof, which also advantageously reduces heat generation on the bone caused by friction while helping to prevent necrosis of the bone. Another advantage of the substantially constant radius R of the inner surface 20 and the radius R' of the outer surface 18 is that the bone saw bit 10 is less likely to impinge upon either piece of a bone during cutting thereby avoiding the ill healing effects caused by necrosis.

Figure 3:
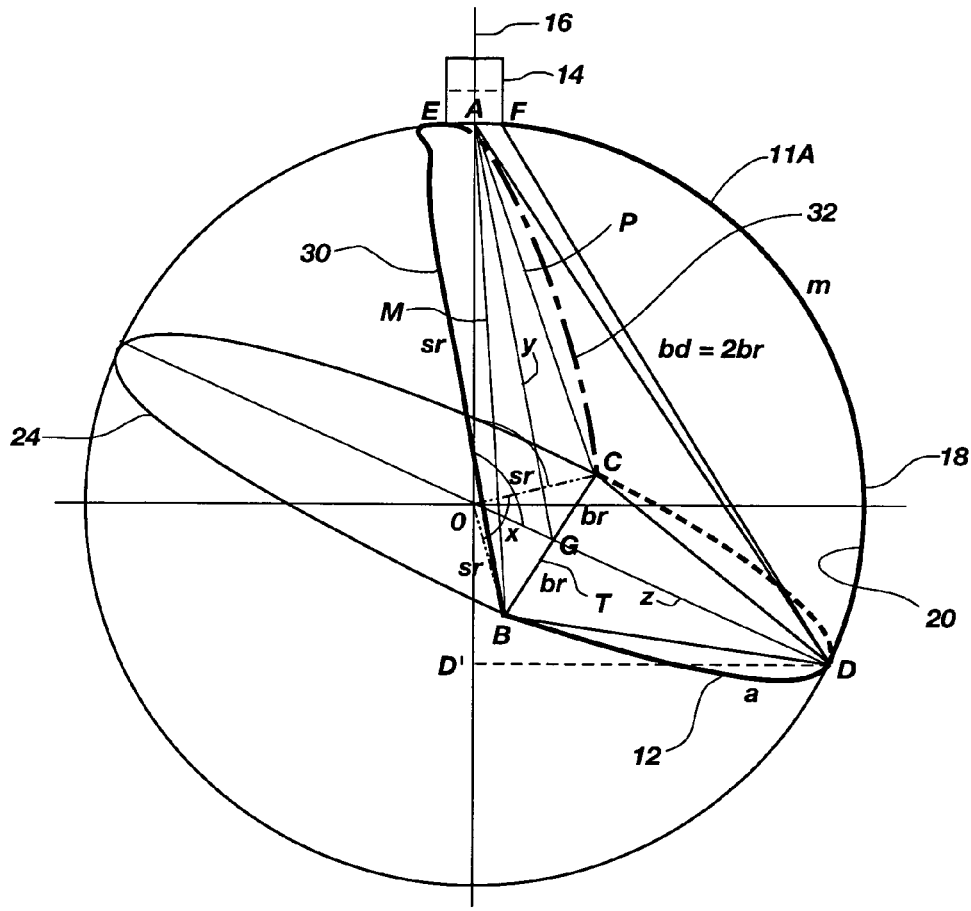
FIG. 3 is a schematic representation illustrating a bone saw bit in accordance with another embodiment of the invention.

With reference also to FIG. 3 and continued reference to FIG. 1, the cutting end 12 of the part spherical body 11 extends as an arc BDC that lies substantially within a plane 24 intersecting the origin O. The arc BDC has a radius SR that is substantially equal to the radius "R" of part spherical body 11 allowing a uniform and non-complex cut to be made by the bone saw blade 10. The radius R and radius R' allow the part spherical body 11 to substantially follow precisely within the path made by the cutting end 12 through the bone substantially without impingement thereupon. The dimensional difference between radius R and the radius R'is the thickness of the bone saw blade 11. While the radius SR of the arc BDC and the radius "R"are substantially equal, it is recognized that they may vary to a slight degree.

Optionally, the cutting end 12 may extend as an arc BDC between the outer surface 18 and the inner surface 20 of the part spherical body 11.

Figure 6A:
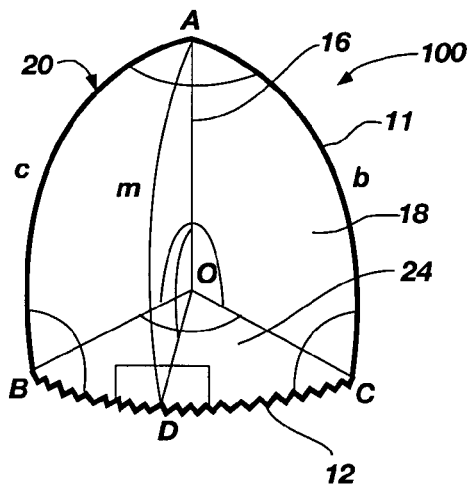
FIGS. 6A-6D show various views of a pictorial representation of a bone saw bit in accordance with yet another embodiment of the invention.
Figure 6B:
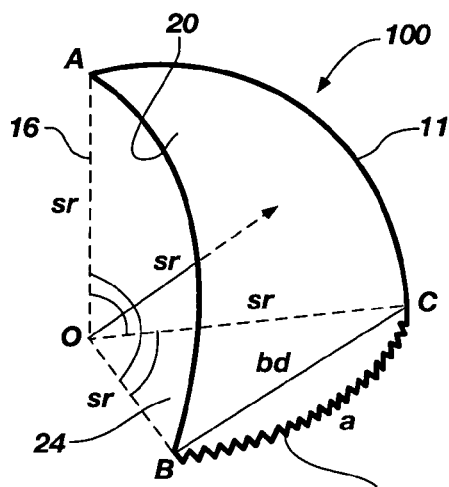
Figure 6C:
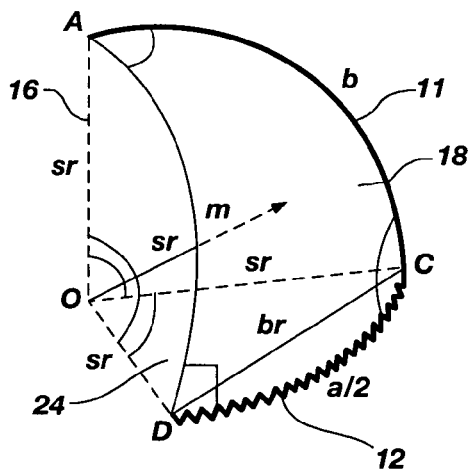
Figure 6D:
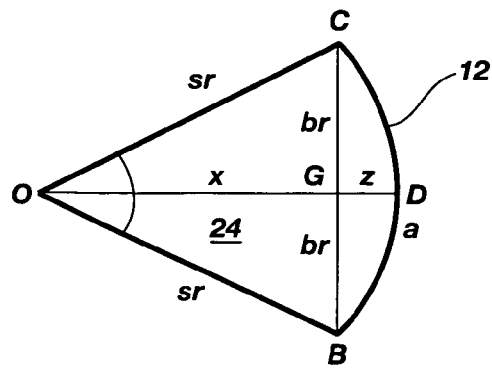

Returning to the bone saw bit 10 of FIG. 1, the bone saw bit 10 has a part spherical body 11. The part spherical body 11 is shaped efficiently to allow the cutting end 12 to engage and cut through a bone at sufficiently steep angle without the bone engaging a substantial portion of the part spherical body 11 or the shank 14 as severance of the bone is completed. In other embodiments, the part spherical body 11 may be contained in less than one hemisphere, in this regard it is a partial hemispherical body. Moreover, the part spherical body 11 may have a shape substantially formed as a spherical triangle (see FIG. 6A), wherein the cutting end 12 is one of the three arcs forming the spherical triangle.

Turning again to FIG. 1, the cutting end 12 comprises a plurality of cutting teeth 26. Each cutting tooth 26 includes oppositely opposed cutting surfaces 27, 28 arranged within a single row. It is to be recognized that other cutting teeth are contemplated within the scope of this invention for example, and without limitation, jagged serration, hyper- or hypo-extending surface edges and multiple rows of cutting teeth. The opposed cutting surfaces 27, 28 of the plurality of cutting teeth are each symmetrically spaced and aligned.

Optionally, the plurality of cutting teeth 26 may also comprise a plurality of inner cutting teeth and a plurality of outer cutting teeth, where the inner cutting teeth each have an inner tooth surface, the inner tooth surface having the radius R of the inner surface 20 of the part spherical body 11, and the outer cutting teeth each having an outer tooth surface, the outer tooth surface congruent with the outer surface 18 of the part spherical body 10.

Figure 4:
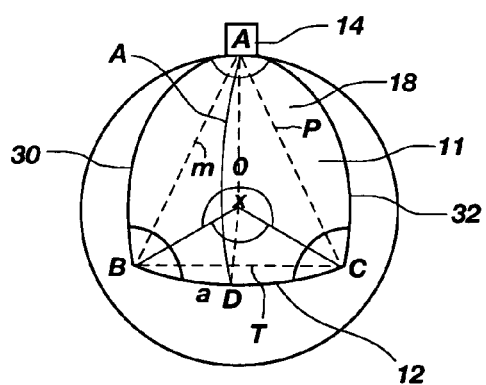
FIG. 4 is a front view of the bone saw bit shown in FIG. 3.

FIG. 3 shows a schematic representation, circumscribed about a sphere, illustrating a bone saw bit 10 in accordance with another embodiment of the invention. Reference may also be made to FIG. 4. The part spherical body 11 includes an outer surface 18, an inner surface 20, a cutting end 12 extending between the outer surface 18 and the inner surface 20, an axis 16 extending from the outer surface 18 through the inner surface 20, and an origin O located on the axis 16. The cutting end 12 extends as an arc BDC lying substantially within a plane 24 intersecting the origin O. An integral shank 14 extends outwardly from the outer surface 18 of the part spherical body 10 and is substantially aligned with and extends parallel to the axis 16.

The part spherical body 11 has a shape substantially formed as a spherical triangle wherein the cutting end 12 is one of the three arcs forming the spherical triangle and the other two arcs are represented by numerals 30 and 32. As shown more specifically by FIG. 4, the spherical triangle is formed by a first arc defined by the cutting end 12, which extends between vertex B and vertex C. A second arc 30 extends from vertex B to vertex A. The third arc 32 extends from vertex A to vertex C. A cord M extends from the vertex A to the vertex B. Similarly, a cord P extends from vertex A to vertex C. In the preferred construction of the invention, cord M is dimensionally equivalent to cord P. A cord T extends from vertex B to vertex C. As further shown in FIG. 3, vertices B and C are each positioned at a radial distance SR from the origin O. A point D is defined as being positioned midway on the arc 12 extending between vertices B and C. The cord T is shown as being formed of two elements, each element being designated BR. The elements BR are dimensionally equivalent to one another. An arc m extends from the vertex A to the point D as shown in FIG. 4. A radius SR extends from the origin O to the point D. The intersection of the radius Z, which extends from the origin O to the vertex D, with the cord T defines a point G. Line Y extends from the vertex A to the point G as shown. Similarly, the line X extends from the origin O to the point G. The inner surface 20 is positioned at a radial distance SR from the origin O. Similarly arc BDC which defines the cutting end of the saw bit, is also positioned substantially at a radial distance defined by the radius SR.

Figure 5:
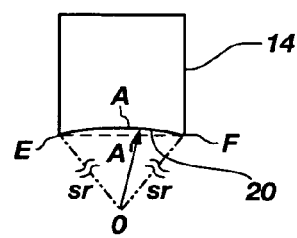
FIG. 5 is a side view of a shank of the bone saw bit shown in FIG. 3.

As shown in FIG. 5, the inner surface 20 of the shank 14 is also disposed at a radial distance corresponding to the length of the same radius SR, which, in addition to the benefits provided herein, allows the bone saw bit 10 to make an efficient cut of a bone by taking advantage of the entire part spherical body 11. As further illustrated in FIG. 5, two reference points E and H are defined at the intersection of opposing edges of the shank 14 and the outer surface 20 of the bit 11.

Figure 3A:
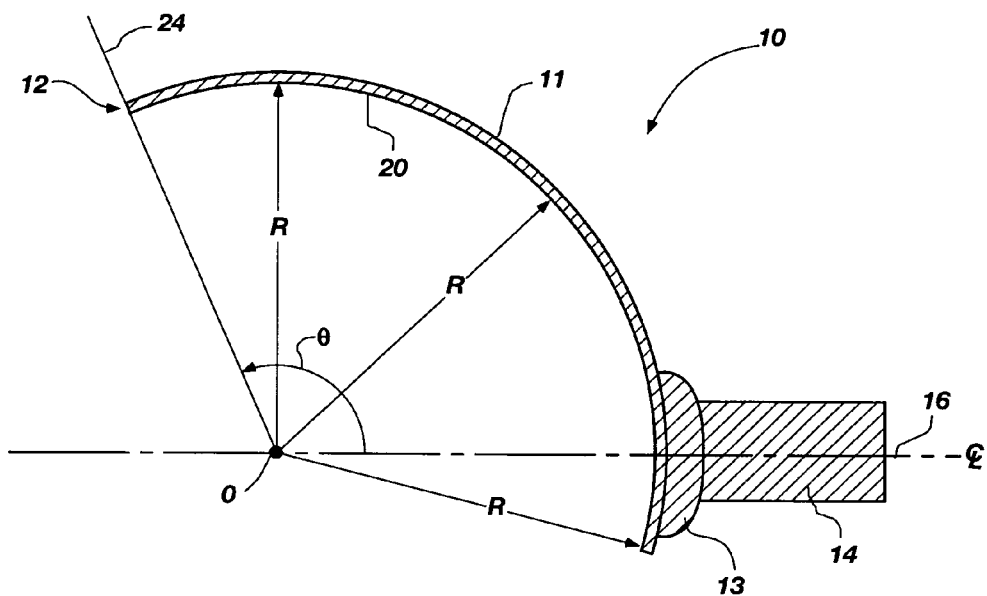
FIG. 3A is a cross sectional view of the bone saw bit of FIG. 3.

Advantageously as shown in FIG. 3, the alternative embodiment of the bone saw bit 11, designated bone saw bit 11A is designed for continuous cutting of a bone when the bone is equal to or smaller in diameter than the length of cord T or 2BR, i.e. the length of a cord between points B and C. In this particular embodiment, the length of cord T is dimensionally less than 2R where R is the length of the radius SR for the inner surface 18 of the bit 11A a previously described. For the illustrated bit 11A, FIGS. 3 and 3A illustrate that the cutting end 12, defined along the arc BDC, lies in a plane 24 which intersects the origin O preferentially and substantially at an angle θ from the axis 16. In FIG. 3A the angle θ is shown as approximately 120 degrees. In preferred embodiments of the invention θ is an angle having a degree measure between 35 degrees and 135 degrees as measured from the axis 16.

FIGS. 6A-D show various views of a pictorial representation of a bone saw bit 100 in accordance with yet another embodiment of the invention. The bone saw bit 100 has a part spherical body 11 that includes a cutting end 12, an outer surface 18, an inner surface 20, an axis 16 extending from the outer surface 18 through the inner surface 20, and an origin O on the axis. The cutting end 12 extends between the outer surface 18 and the inner surface 20 of the part spherical body 11 and substantially lies within a plane 24 intersecting the axis 16. The cutting end forms an arc BDC. The plane 24 is aligned approximately 120 degrees to the axis 16 and intersects the origin O in this embodiment allowing the cutting end 12 to efficiently cut or surgically sever a bone into two pieces having convex and concave domes, respectively.

Optionally, the plane 24 containing the cutting end 12 may intersect the axis 16 at a location positioned between the origin O and the point A. Where the plane 24 intersects the axis 16 at a location between the origin O and the point A, the radius of the cutting end 12 will have an effective radius equal to the radius SR of the inner surface 20 of the part spherical body 11 allowing for the same "dome" osteotomy to be performed even though the theoretical radius is potentially smaller than the actual radius SR of the inner surface. To obtain the effective radius, a surgeon, for example, may have to rotate the saw blade bit 100 about a greater circle while completing an operation (to be described below). Conventional saw blades can not complete this type of "dome" osteotomy because the cutting end resides in a plane that is below the origin which will cause, as described above, the blade to become wedge between the pieces of a bone being severed or cause damage thereto during severance.

Optionally, plane 24 containing the cutting end 12 of the bone saw bit 100 that intersects the axis between the origin O and the inner surface 20 and may lie substantially between 35 degrees and 135 degrees from the axis 16. While the plane 24, in this embodiment of the invention, may lie at angles greater than 135 degrees, it is expected that this to may cause undesirable binding of the bone saw bit 100 between the bone pieces being cut as described above. The plane 24 may lie with respect to the axis 16 to a lesser extent than the 35 degrees described herein without consequence, but becomes less effective for cutting bones.

In still other embodiments of the invention, a plane containing the cutting end and intersecting the axis between the origin and the inner surface may be substantially perpendicular to the axis in order to achieve greater cutting surface area of a bone while making a dome osteotomy with cutting radius SR.

As with the other embodiments of the invention, the cutting end 12 may also comprise a plurality of cutting teeth. The cutting end 12 may include other cutting structures suitable for cutting material, such as bone, as would be recognized by a person having ordinary skill in the art.

Figure 7:
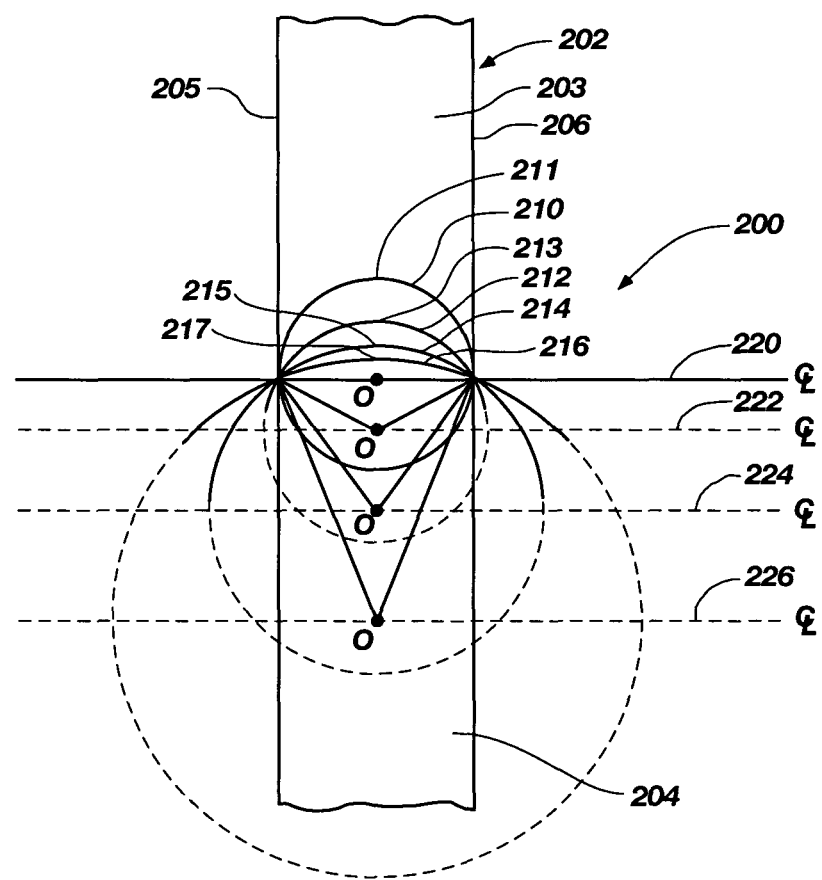
FIG. 7 is a graphical view showing dome heights in a bone for various sized bone saw bits in accordance with embodiments of the invention.

FIG. 7 shows a graphical view 200 of various dome heights 211, 213, 215, 217 achieved in a bone 202 using various sized bone saw bits 210, 212, 214, 216, respectively, in accordance with embodiments of the invention.

Each of the bone saw bits 210, 212, 214, 216 comprise a part spherical body 11 having an outer surface 18, an inner surface 20, a cutting end 12 extending as an arc "BDC" between the outer surface 18 and the inner surface 20, an axis 16 extending from the outer surface 18 through the inner surface 20, and an origin O on the axis 16, the inner surface 20 and the arc BDC have a radius R or SR extending from the origin O as described in FIGS. 1-6.

The bone 202 includes surgically severed bone portions 203 and 204. The bone portion 203 is a concave dome and the bone portion 204 is a convex dome. Each of the dome heights 211, 213, 215, 217 achieved by using various sized bone saw bits 210, 212, 214, 216, respectively, are shown between the outer edges 205, 206 of the bone, but include for illustrative purpose the entire circular envelope represented by the cutting radius SR.

The dome height 211 is achieved by using the bone saw bit 210 having radius SR that is exactly one half the width of the bone 202 and a cutting end 12 that has an arc BDC. In order to sever the bone 202 into portions 203, 204, the bone saw bit 210, while engaging the bone, is rotated about cutting center point 220. The center point 220 is representative of the center point about which the bone saw bit may be rotated while cutting a bone and may remain stationary or transition with respect to the bone depending upon the cut being made. In this respect, the cutting center point 220 generally denotes a floating point about which the tool may be rotated by a surgeon. The dome height 211 is the theoretically largest dome height obtainable and requires precise control by a surgeon in order to accomplish the osteotomy, particularly considering that the cutting end may interfere with opposing bone portions and due to interference from the hub it may be difficult to accomplish.

The dome heights 213, 215, 217, obtained by using larger more forgiving bone saw bits 212, 214, 216, range between approximately 75% and 25% of maximum dome height 211. However, greater or lesser dome height may be obtained by using other sized bone saw bits. Each of the bone saw bits 212, 214, 216 have a cutting end 12 with an associated cord BDC substantially equal or greater than the diameter of the bone. As is shown in the illustration of FIG. 7, bone saw bits 212, 214, 216 are each rotated about center points of rotation 222, 224, 226, respectively, in order to complete severance of the bone 202.

It is to be recognized that the greater the dome height, such as dome heights 211, 213, 215, 217, the greater the surface or contact area for bone portions 203 and 204 when repositioned in any of the three degrees of freedom mentioned above. Also, "true dome" osteotomies described herein provide for the optimal contact or surface area for each bone portion 203, 204 for any given dome height.

Generally in the embodiments of the invention, the thickness of the part spherical body 11 between the inner surface 20 and the outer surface 18 is mostly constant. However, it is recognized that the part spherical body 11 may include corrugations, ribs, cutouts or low friction coatings on or between either of the inner surface 20 and the outer surface 18 in order to enhance the cutting efficiency of the bone saw bit or to minimize heat generation thereby minimizing necrosis of the bone. Corrugations, cutouts and ribs may act as channels for allowing a cooling fluid to be directed towards the cutting end of the bone saw bit during a surgery to further facilitate the minimization of heat generation. Another aspect of the bone saw bit is it will be self-guiding and self-centering while cutting bone, because of its substantially spherical design.

In still other embodiments of the invention, the bone saw bit may include a balance member coupled to a portion of the part spherical body, such as the hub, and or the shank in order to balance the bone saw bit about the axis of oscillatory motion. By providing a balance member, the vibration is minimized during a cutting proceeding that facilitates manipulation and control of the bone saw bit by the surgeon.

It is to be recognized that the bone saw bit 10 as shown in FIG. 1 includes the cutting end 12 that lies substantially in a plane that intersects the origin O. In this regard, the cutting end 12 lies substantially about a great circle of the bone saw bit 10, which advantageously allows the bone saw bit 10 to be used with an oscillating saw having any magnitude of oscillatory motion consistent for use with the invention.

FIGS. 8A-E illustrates an embodiment of the instant method of performing an osteotomy of a bone 202. Initially, a bone saw bit 212 as described above with respect to FIG. 7 is provided. The user determines the location of the spherical center or origin O of the bone saw bit. Next, the user identifies a longitudinal or central axis 201 of the bone 202 to be sectioned. A location 203 on the outer surface of the bone 202 where the cut is to be initiated is next identified. Alternatively, the apex 223 of the anticipated cut may be identified.

Utilizing the location of the origin O relative to the cutting end 12 of the bone saw bit 212, i.e. the radius SR, and the location of the longitudinal axis 201, the user calculates the location of a center of rotation 222 for the bone saw bit 212 for the anticipated sectioning. The center of rotation is typically located at a radial distance W from either the location 203 or the apex 223. Radial distance W typically corresponds to the length of the radius SR of the bone saw bit. In many instances, the center of rotation 222 will be located on the longitudinal axis 201 of the bone 202. In the embodiment of the method shown in FIGS. 8A-E, the center of rotation 222 is positioned on the longitudinal axis 201 at a location 207 wherein the radial distance W is substantially identical to the length of the radius SR of the saw bit 212.

Figure 8A:
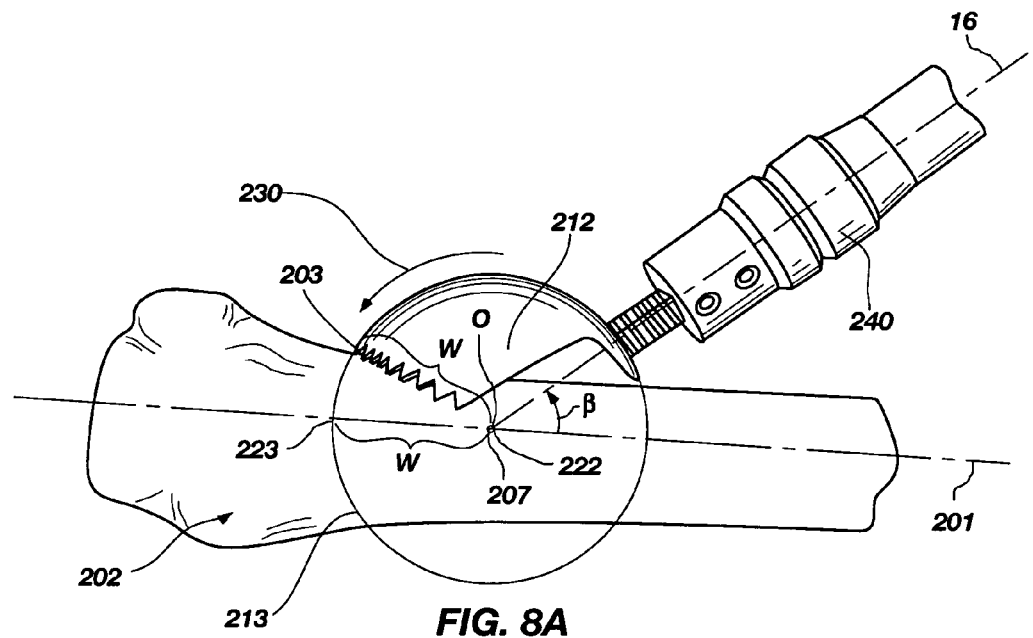
FIGS. 8A-8E showing osteotomy of a bone using a bone saw bit in accordance with the invention.
Figure 8B:
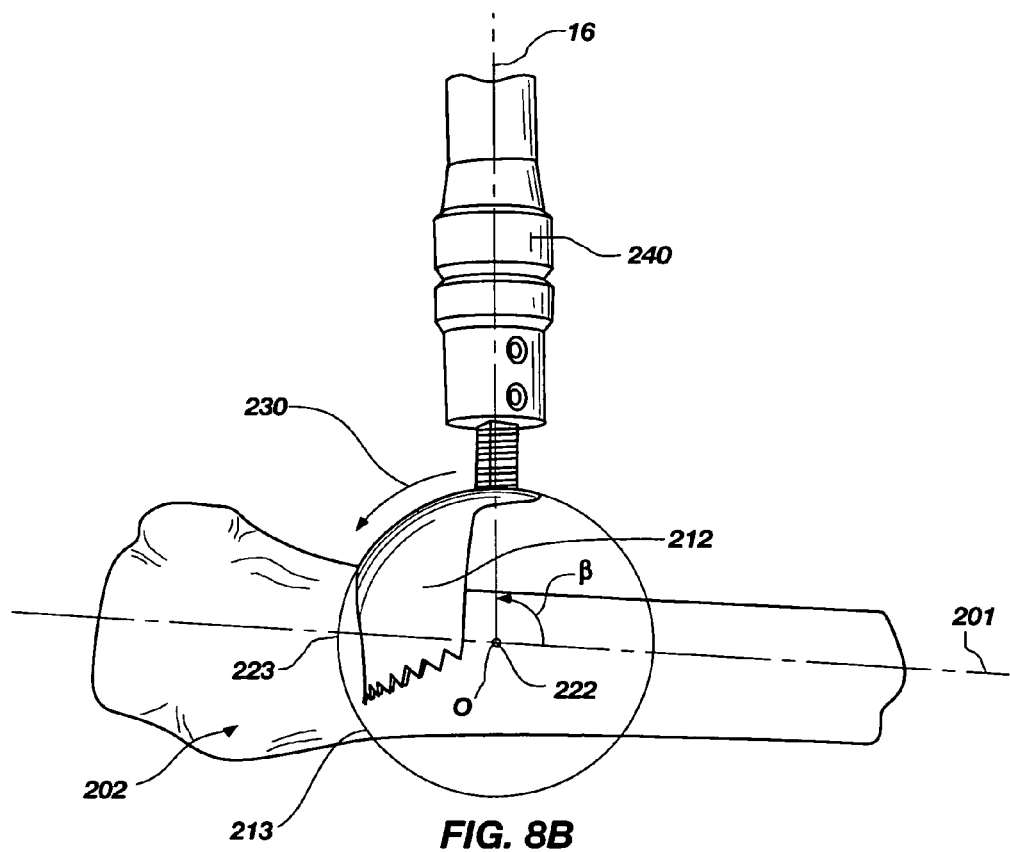

Having identified the point 207 and determined the orientation of the center of rotation 222, the bone saw bit 212 is then positioned on the bone 202 in an orientation and angle β predetermined by the surgeon such that the bone saw bit 212 may be rotated as shown by arrow 230 to produce dome height 213. In one embodiment of the invention as illustrated in FIG. 8A, the origin O of the bone saw bit is positioned at the point 207.

In this embodiment the center of rotation 222 may be determined by utilizing the methodology for determining the location of a center of rotation of angulation as described in Principles of Deformity Correction, New York: Springer, 2005, by Dror Paley and Contributor J. E. Herzenberg, the text of which is hereby incorporated by reference. Specific reference is made to pages 61 et seq. of the Paley book wherein a method of determining a CORA (center of rotation of angulation) for a deformed bone is described. The Paley methodology utilizes a visualization of a deformed bone, which has been divided into segments. The segments are visualized as being angulated to an orientation, which will meet the objectives of the surgeon user. Each of the segments defines a respective longitudinal axis, i.e., respectively a proximal longitudinal axis for one segment and a distal longitudinal axis for the other segment. In the visualized orientation, the pair of proximal and distal longitudinal axes intersect and form an angle. The point at which the proximal and distal axis lines intersect is called the center of rotation of angulation (CORA). In one embodiment of the method of the instant invention, the Paley method for determining the CORA of a subject bone is utilized as a means of locating a CORA which is then used as the center of rotation 222 for purposes of the instant method, i.e., once the location of the CORA is identified utilizing the method of Paley the location of the CORA may be used for purposes of the instant method by either locating the center of rotation point 222 at the same location as the CORA or alternatively, the CORA may be utilized to otherwise identify a location 203 or 233 at which the sectioning should preferably be performed. Should the user adopt the latter approach, the above described methodology may be then employed to determine the location of the center of rotation 222.

The driver 240, an oscillating or reciprocating saw of a type conventionally associated with surgical saws, is then energized to actuate, i.e. oscillate the cutting end of the bone saw bit 212. The bone saw bit 212 having been positioned at the initial angle β determined by the surgeon relative to the center of rotation 222 such that the origin O of the bit is positioned on or substantially on the point of intersection of the center of rotation 222 and the longitudinal axis 201 engages the bone 202 at point 203 and thereafter is rotated about the center of rotation 222 to cut a path (represented by the dome height 213) by pitching or rotating the driver forward and downward.

In the embodiment of the instant method illustrated in FIGS. 8A-E, the center of rotation 222 remains spatially fixed throughout the procedure.

Advantageously, the surgeon will control the orientation of the saw, while the bone saw bit 212 will guide or self-guide and self center itself while making the dome shaped cut between opposing portions 203, 204 of the bone. The procedure is completed when the bone saw bit 212 cuts through the bone 202. In this osteotomy example, bone saw bit 212 is properly sized allowing the positional angle β at the beginning of the cut to be approximately 35 to 45 degrees with respect to the longitudinal axis 201 of the bone 202, which allows the bone saw bit 212 to be rotated through about 135 to 145 degrees in order to finish cutting the bone 202.

Figure 8C:
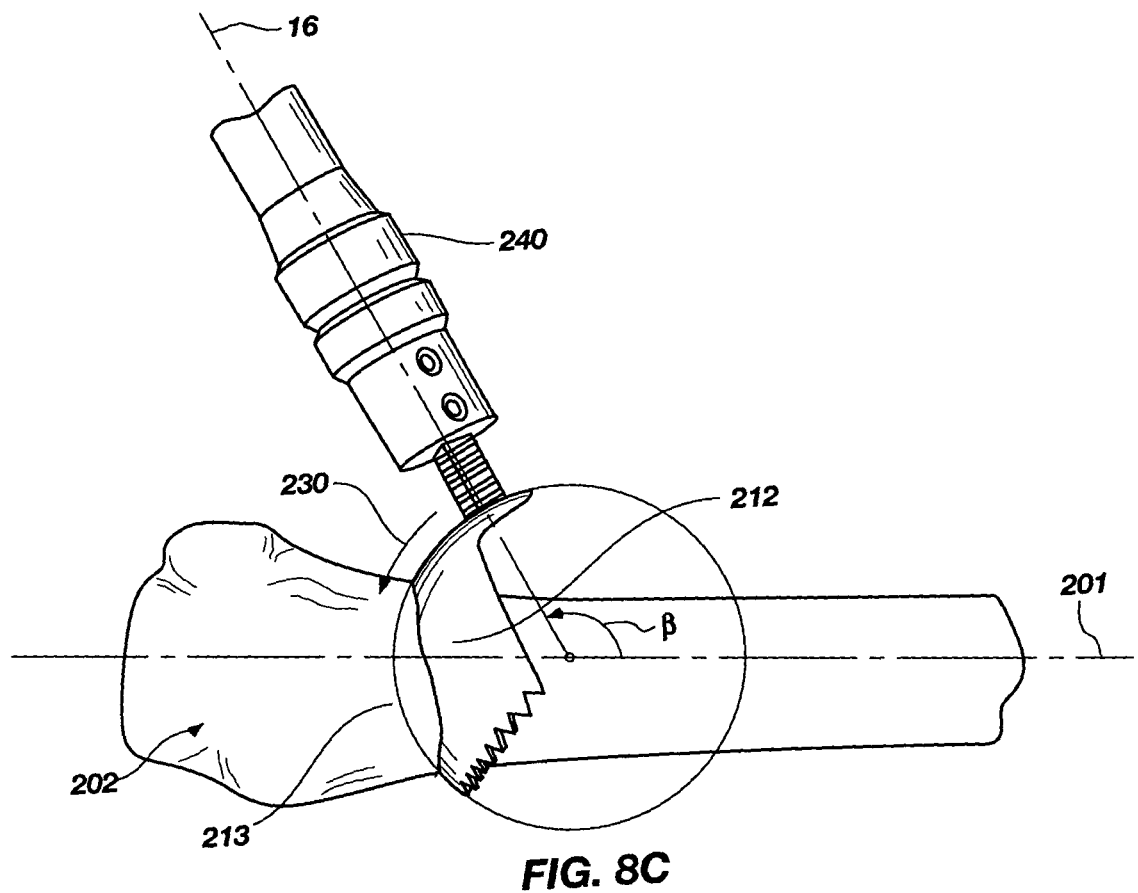
Figure 8D:
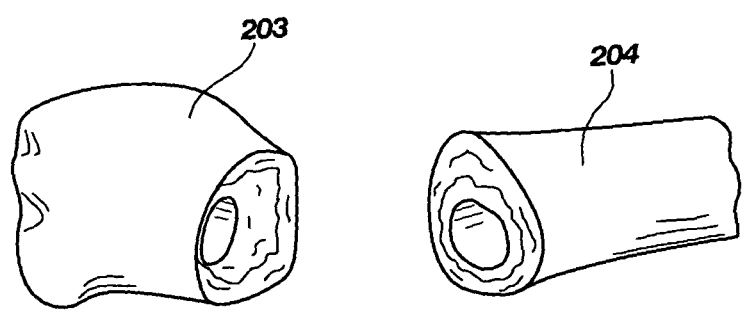
Figure 8E:
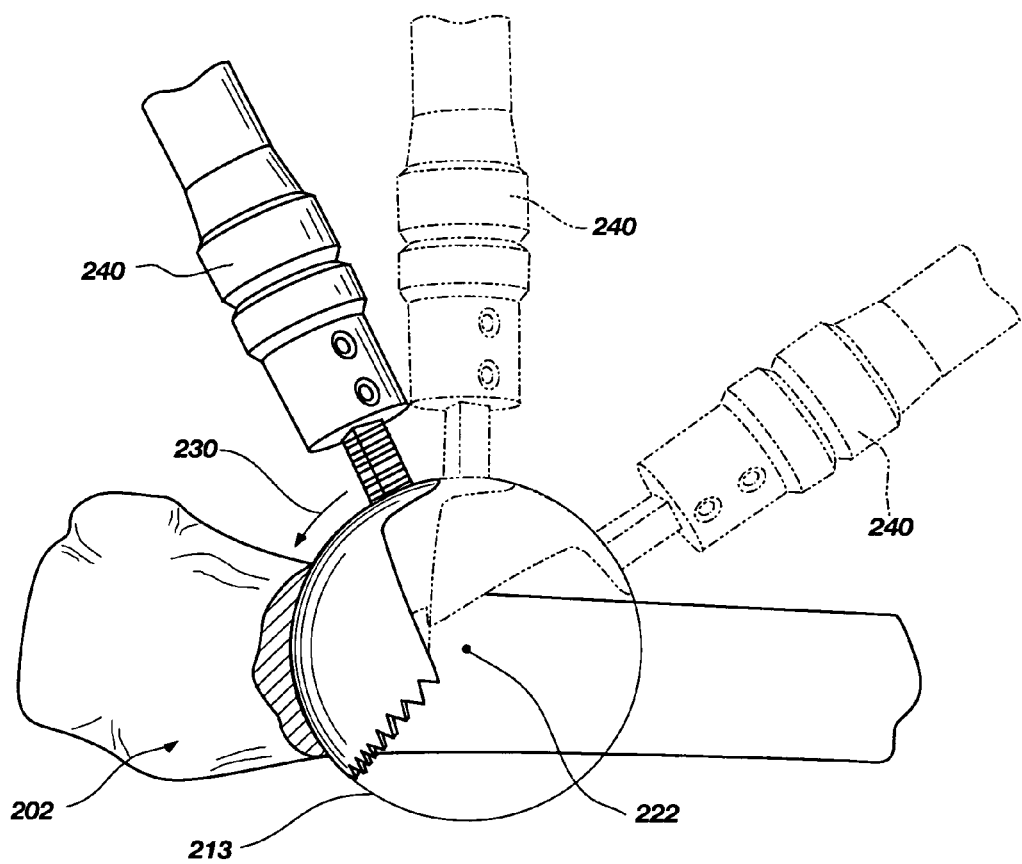

In order to balance the need for efficient cutting, the need to sever the bone in a single pass and the need to provide three dimensional adjustment of the bone pieces, the cutting plane may intersect the origin O at a greater or lesser angle than the 120 degrees illustrated in FIG. 8C.

Figure 9:
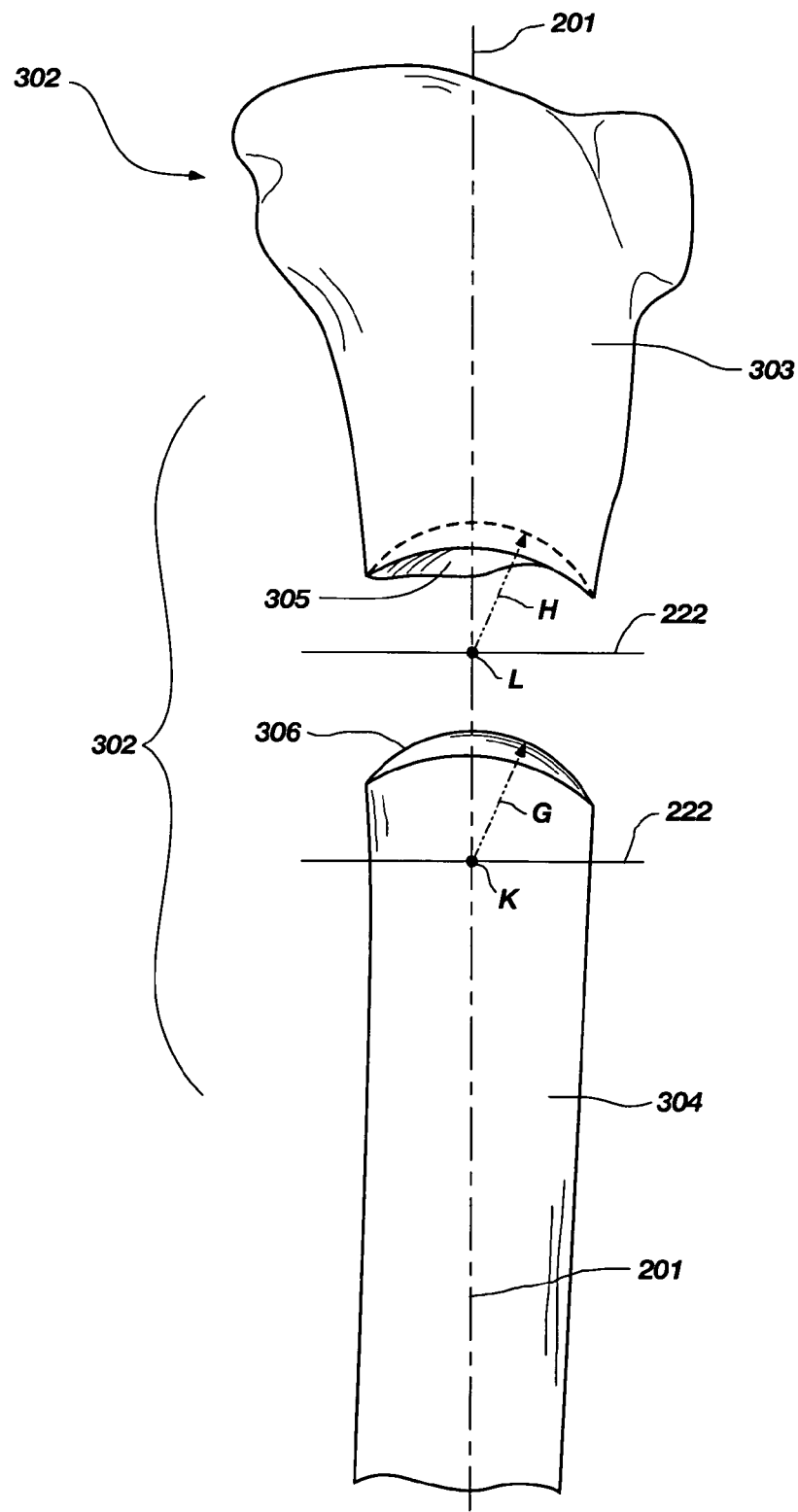
FIG. 9 shows two bone portions resulting from "true dome" osteotomy.

FIG. 9 shows two bone portions 303, 304 of a bone 302 having "true dome" or spherical osteotomy surface having been surgically severed with a saw blade bit. Bone portion 303 includes a concave surface 305 defined by the radius J extending from an origin L that corresponds to center of rotation 222 and the axis 201 of the bone 303. Bone portion 304 includes a convex surface 306 defined by the radius G extending from an origin K that corresponds to central point 222 and the longitudinal axis 201 of the bone 304. It is to be recognized that the origins L and K may extend from a location other than the longitudinal axis 201 of the bone or the center of rotation 222 depending upon how the surgeon makes the cut through the bone with a bone saw bit. The bone 302 was severed into bone portions 303, 304 with a bone saw bit in accordance with embodiments of the invention as the surgeon transitioned the bone saw bit about point 222 as described above.

Advantageously, the concave surface 305 substantially mates with the convex surface 306 allowing the bone portions 303, 304 to be repositioned together about any of three degrees of freedom, because the concave surface 305 and the convex surface 306 are both "true dome" or spherical osteotomies that substantially mate. Furthermore, the surgeon may perform the osteotomy by positioning the central point 222, or allowing it to transition, where it is convenient to sever the bone 302, because the "true dome" or spherical osteotomy result is obtained anywhere about the bone, particularly their central axis, when the novel bone saw bit is used.

Figure 10:
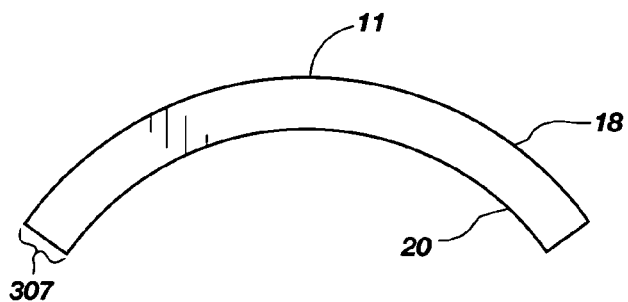
FIG. 10 is a front view of a bone saw bit of the instant invention.
Figure 11:
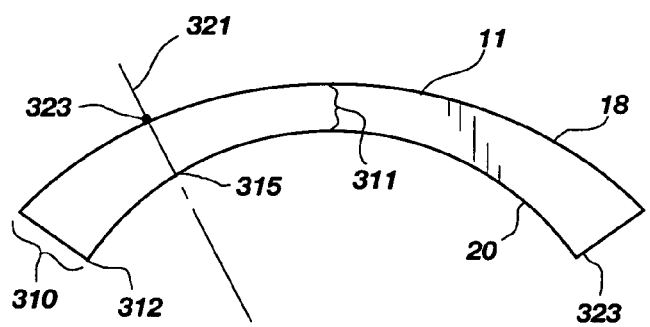
FIG. 11 is a front view of an alternative bone saw bit of the invention.
Figure 12:
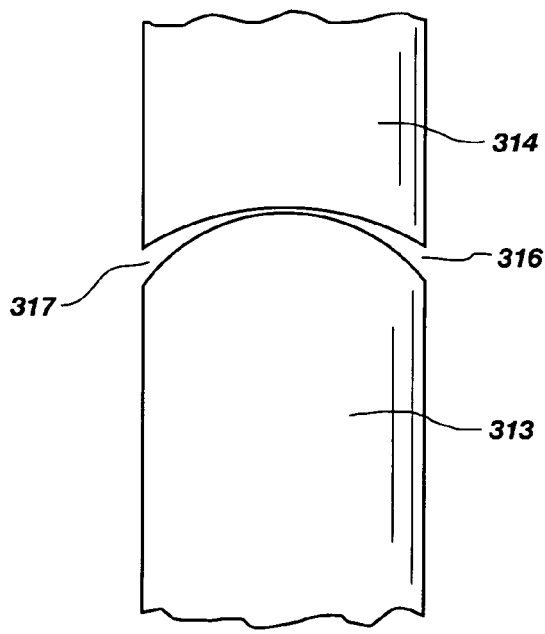
FIG. 12 is a sectional side view of a bone which has been sectioned by use of the alternative bone saw bit of FIG. 11.

FIGS. 10-12 illustrate an alternative embodiment of the invention wherein the thickness of the bit 11 is altered from the bit constructions described above. As shown in FIG. 10 a saw bit of the constructions heretofore described has a constant thickness 307 over its entire length. Stated otherwise, the distance between the inner surface 20 and the outer surface 18 remains constant over the body of the bit. The bit shown in FIG. 11 alters this construction in that the thickness 310 of the bit proximate the opposing ends 312 and 323 of the bit 11 is dimensionally larger than the thickness 311 of the bit proximate the central region of the bit. As shown, in this embodiment, the inner surface 20 is configured as a smooth curved surface. In this construction, the radius of curvature of a location 315 on the inner surface 20 typically has a smaller radius of curvature than a corresponding location 323 on the outer surface 18 positioned along a radial line 321.

The bit 11 of FIG. 11 may be utilized in the instant invention to produce a bone sectioning of the configuration shown in FIG. 12. As shown a bone has been sectioned into two elements 313 and 314, utilizing the bit of FIG. 12. The upper surface configuration of the element 313 exhibits a surface which does not have a constant radius of curvature over its entire surface. Indeed, as can be noticed, the edges 316 and 317 of the upper region of the bone 313 have a much smaller radius of curvature than their counterpart surfaces on the sectioned portion of bone 314. As shown in FIG. 12, the radius RR from the origin O or point of rotation 222 is dimensionally larger than either of the radii RT which extend from the origin O to either of the edges of the upper sectioned end of the bone 313. This particular configuration may prove useful in certain circumstances, notably in acute angular correction where the friction between bone sections may be high enough to prevent proper positioning.

Figure 13:
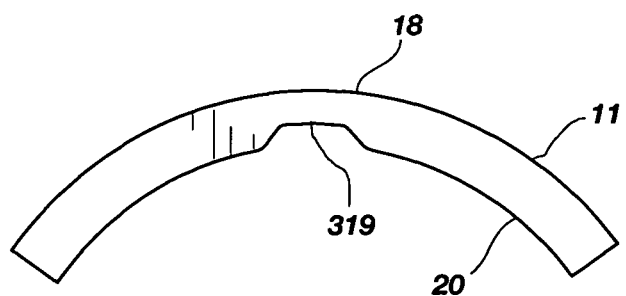
FIG. 13 is a front view of a second alternative bone saw bit of the invention.
Figure 14:
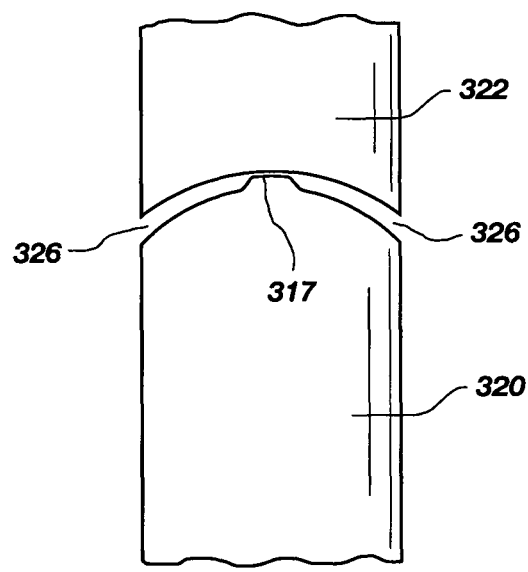
FIG. 14 is a sectional side view of a bone which has been sectioned by use of the second alternative bone saw bit of FIG. 12.

FIGS. 13 and 14 illustrate a further embodiment of the invention wherein the inner surface 20 of the bit 11 is configured to define a recess 319. In the illustrated embodiment of the bit, the thickness of the bit 11 remains constant over the length of the bit with exception of the region defining the recess. In use the bit of FIG. 13 will produce a section configuration corresponding to FIG. 14 in which the bone element 320 will define an upstanding ridge 317 and corresponding voids 326 on either side of the ridge which separate the two bone elements from one another.

In acute angular correction where the friction between bone sections is high enough to prevent proper positioning.

Figure 15:
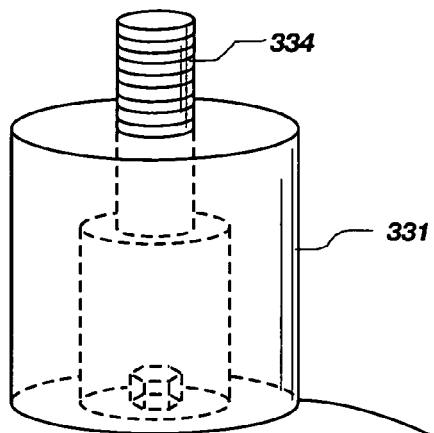
FIG. 15 is a perspective view of a connection structure for securing a bone saw bit of the invention to an actuating device.
Figure 15A:
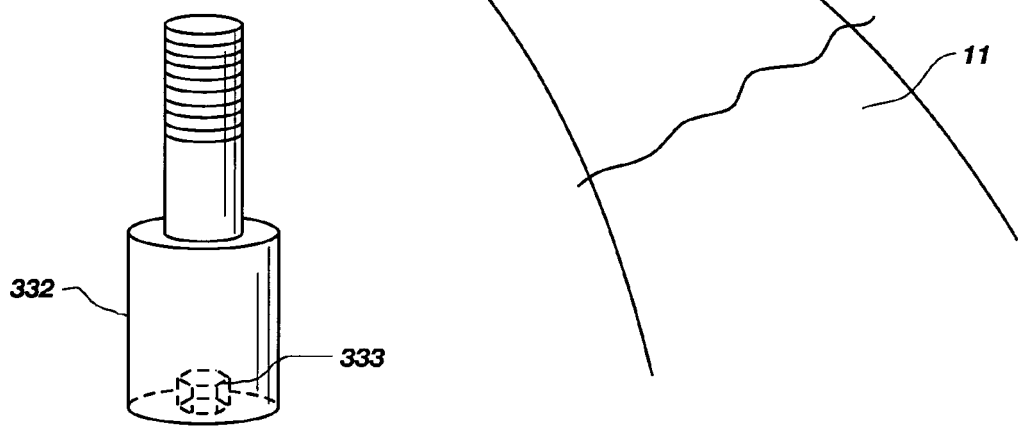
FIG. 15A is a perspective view of a connection element of the connection structure of FIG. 15 is a sectional.
Figure 16:
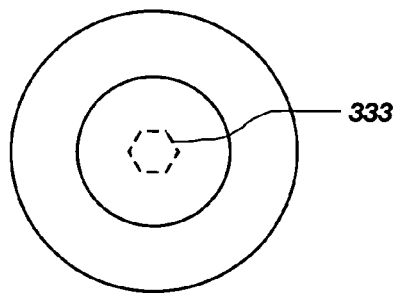
FIG. 16 is an end view of the connection structure of FIG. 15A.

FIGS. 15 and 16 illustrate a structure for interconnecting the bit 11 of the invention with an actuating device (not shown). The end of the bit 11 is shown coupled with a connection structure which includes a threaded shaft 334 adapted for coupling with an actuating device of the type conventionally used with surgical saws. A housing 331 defining a void therein configured to receive a threaded element 332 is positioned on the bit 11. Element 332 defines a cavity 333 therein dimensioned to receive a connection nut secured to the bit 11. FIG. 16 is a top view of the element 332.

While embodiments of the invention have been described generally with respect to part hemispherical body, a spherical body and a sphere, it is to be recognized that a prolate or oblate spheroid shape may also be used with the teaching disclosed herein.

The bone saw bit in accordance with the embodiments described above may be used to make "true dome" or dome-shaped cuts in solid materials, but are preferentially directed toward making dome-shaped cuts in bones, such as dome osteotomies. The bone saw bit has many applicable uses including osteotomy procedures in both veterinary and human medicine/surgery.

The saw blade bit may be provided for disposable or reusable uses and may be available in sterile or non-sterile conditions. The saw blade bit described herein is not limited to the specific applications disclosed, but may be utilized for many types of surgical procedures in humans and animals requiring the severing, cutting or removing sections of anatomical structures, including but not limited to: general long bone osteotomies for correction of angular deformities, resection of the diseased bone area or section between two joints of the same bone, osteotomy of bones with malunions after improper healing of fractures, osteotomy for proximal humeral deformity correction, distal humeral osteotomy for correction of cubitus varus, osteotomy of distal humerus for correction of medial compartmental disease of the elbow, osteotomy of the distal radius for correction of premature physeal closure of the ulna and/or radius, periacetabular osteotomy for the correction of hip dysplasia, proximal femural osteotomy for correction of hip dysplasia and femoral head and neck angle correction, distal femoral and supracondylar osteotomy, proximal tibial and high tibial osteotomy for unicompartmental disease correction and valgus varus correction, calcaneal osteotomy, proximal metatarsal osteotomy, Tibial Plateau Leveling Osteotomy (TPLO) etc. The saw blade bit may be of any size and preferably constructed of stainless steel.

Generally, the invention provides a saw blade bit, and method therewith, that provides for cutting true dome shape surfaces, is self-guiding, aides healing, minimizes damage to surrounding soft tissue by self-centering, as well as provides for maximum contact of the substantially mating surfaces, optimal dome height, enhanced stability and adjustability.

The saw blade bit described above may come in different sizes and attachment configurations for use with different bone sizes and surgical procedures. The saw blade bit may be assembled into kits. The kits may further include tools associated with the blades, such as various handles, screws, clamps, locking mechanisms, fastening devices, measuring devices, brackets, power tools, etc.

Also, the saw blade bit may be used to make dome shaped or substantially spherical cuts through solid substance.

From the foregoing the invention provides a novel device and method to perform "true dome" or spherical osteotomies. The invention attains several advantages, some of which are summarized as follows: it is an advantage of the invention to provide a device and method for making a dome shaped cut through a solid substance resulting in two substantially congruent mating surfaces, and more specifically a device and method to perform true dome osteotomies as opposed to conventional barrel-vault osteotomies for the purpose of correcting malalignment and malorientation of bones in humans and animals. Another advantage of the invention is to provide a dome saw blade and method to perform improved corrective osteotomies that produce two bone sections with congruent dome shaped mating surfaces that may be realigned and fixation applied as understood by a person having skill in the art, and which may provide for optimal dome height, increased stability of the rejoined bone sections, minimized bone loss, decreased chance of damage to bone tissue and the surrounding soft tissue, rapid and structurally effective mending or knitting of the bone, faster and more reliable healing, as well as the orthopedic surgeon's ability to make intraoperative adjustments to attain the desired correction, including correcting for large rotational deformities.

Changes may be made to the embodiments described in this disclosure without departing from the broad inventive concepts they illustrate. Accordingly, this invention is not limited to the particular embodiments disclosed, but is intended to cover all modifications that are within the scope of the invention as defined by the appended claims.

What is claimed is:

1. A method of using a spherical osteotomy device for performing spherical osteotomies, the method comprising:
    defining a center point of rotation through a single bone to be sectioned; oscillating a cutting end of the spherical osteotomy device about an origin of the spherical osteotomy device with a driver operably secured to the spherical osteotomy device; engaging the cutting end of the spherical osteotomy device with the bone to be sectioned; sectioning the single bone, in a single pass of the spherical osteotomy device through the single bone, by passing the cutting end of the spherical osteotomy device through the bone while rotating the spherical osteotomy device and the driver about the center point of rotation to form two bone sections from the single bone, the sectioning comprising: forming a first bone section of the two bone sections to have a convex surface having a constant radius from the center point of rotation; and forming a second bone section of the two bone sections to have a concave surface having a constant radius from the center point of rotation;
    self-guiding the spherical osteotomy device through the single bone by rotating an inner surface of the spherical osteotomy device having a constant radius from the origin of the spherical osteotomy device along a portion of the single bone through which the cutting end of the spherical osteotomy device has already passed; and
    reorientating the first bone section and the second bone section at a desired alignment relative to each other in three-dimensions without a gap between the first bone section and the second bone section in a direction along the length of the bone.

2. The method of claim 1, further comprising:
    defining a longitudinal axis of the bone to be sectioned;
    defining a proximal longitudinal axis line and a distal longitudinal axis line;
    determining an intersection of the proximal and distal axis lines, said intersection being denominated as a center of rotation of angulation (CORA);
    deteimining a point of intersection of the CORA and the longitudinal axis of the bone; and
    generally aligning the origin of the spherical osteotomy device with the CORA and the longitudinal axis by orienting the sectioning blade to position the origin of the spherical osteotomy device on said CORA.

3. The method of claim 1, further comprising restricting oscillatory motion of the spherical osteotomy device to a plane containing the cutting end of the spherical osteotomy device.

4. The method of claim 1, further comprising selecting the spherical osteotomy device to exhibit a spherical triangle shape formed by a portion of a surface of a sphere bounded by three arcs of great circles of the sphere where the cutting end is formed by and extends along a boundary of the device formed by one of the three arcs of great circles bounding the spherical triangle shape of the spherical osteotomy device.

5. The method of claim 1, further comprising selecting an entirety of an inner surface of the spherical osteotomy device to exhibit a constant radius from the origin of the spherical osteotomy device.

6. The method of claim 1, further comprising balancing the spherical osteotomy device with a balance member coupled to the spherical osteotomy device.

7. The method of claim 1, further comprising selecting the center point of rotation to substantially coincide with the origin of the spherical osteotomy device.

8. The method of claim 1, further comprising selecting a surface extending along an entirety of the cutting end of the spherical osteotomy device and extending between an inner surface of the spherical osteotomy device and an outer surface of the spherical osteotomy device to extend along a plane intersecting the origin of the spherical osteotomy device.

9. The method of claim 1, further comprising positioning a longitudinal axis of a shank of the spherical osteotomy device coupled to the driver at an angle between 35 degrees and 45 degrees relative to a longitudinal axis of the bone to be sectioned.

10. The method of claim 1, further comprising cutting the bone to be sectioned with an arcuate inner surface of cutting teeth at the cutting end of the oscillating spherical osteotomy device.

11. The method of claim 1, further comprising cutting the bone to be sectioned with an arcuate inner surface of cutting teeth at the cutting end of the oscillating spherical osteotomy device formed by and extending along a boundary of the device formed by one of three arcs of great circles of a sphere bounding a spherical triangle shape of the spherical osteotomy device formed by a portion of a surface of the sphere.

12. The method of claim 1, further comprising rotating an inner surface of the spherical osteotomy device along a portion of the bone to be sectioned through which the cutting end of the spherical osteotomy device has already passed, an entirety of the inner surface having a constant radius from the origin of the spherical osteotomy device.

13. The method of claim 1, further comprising rotating the spherical osteotomy device between 135 degrees to 145 degrees about the center point of rotation to section the bone.

* * * * *

UNITED STATES PATENT AND TRADEMARK OFFICE
CERTIFICATE OF CORRECTION

PATENT NO.        : 8,518,045 B2                                            Page 1 of 1
APPLICATION NO.   : 13/136243
DATED             : August 27, 2013
INVENTOR(S)       : Zsigmond Szanto It is certified that error appears in the above-identified patent and that said Letters Patent is hereby corrected as shown below:

In the claims:

| | | | |
|---|---|---|---|
| CLAIM 1,  | COLUMN 15, | LINE 62, | change "the bone" to --the single bone-- |
| CLAIM 2,  | COLUMN 16, | LINE 20, | change "the bone" to --the single bone-- |
| CLAIM 4,  | COLUMN 16, | LINE 39, | change "arcs of great circles of" to --arcs of-- |
| CLAIM 4,  | COLUMN 16, | LINE 41, | change "of great circles" to --that lies a great circle-- |
| CLAIM 5,  | COLUMN 16, | LINE 44, | change "of an" to --of the-- |
| CLAIM 9,  | COLUMN 16, | LINE 62, | change "the bone" to --the single bone-- |
| CLAIM 10, | COLUMN 16, | LINE 65, | change "bone" to --single bone-- |
| CLAIM 11, | COLUMN 17, | LINE 2,  | change "bone" to --single bone-- |
| CLAIM 11, | COLUMN 17, | LINE 5,  | change "arcs of great circles of" to --arcs of-- |
| CLAIM 12, | COLUMN 17, | LINE 9,  | change "rotating an" to --rotating the-- |
| CLAIM 12, | COLUMN 17, | LINE 11, | change "the bone" to --the single bone-- |
| CLAIM 13, | COLUMN 17, | LINE 17, | change "the bone" to --the single bone-- |

Signed and Sealed this
Eighth Day of September, 2015

Michelle K. Lee
*Director of the United States Patent and Trademark Office*